US006915802B1

(12) United States Patent
Anderson et al.

(10) Patent No.: US 6,915,802 B1
(45) Date of Patent: Jul. 12, 2005

(54) MEDICAMENT PACK

(75) Inventors: Gregor John McLennan Anderson, Ware (GB); Duncan Robertson, Perth (AU)

(73) Assignee: SmithKline Beecham Corporation, Philadelphia, PA (US)

(*) Notice: Subject to any disclaimer, the term of this patent is extended or adjusted under 35 U.S.C. 154(b) by 142 days.

(21) Appl. No.: 10/110,612

(22) PCT Filed: Oct. 11, 2000

(86) PCT No.: PCT/EP00/09992

§ 371 (c)(1),
(2), (4) Date: Apr. 15, 2002

(87) PCT Pub. No.: WO01/28616

PCT Pub. Date: Apr. 26, 2001

(30) Foreign Application Priority Data

Oct. 16, 1999 (GB) ..................................... 9924415

(51) Int. Cl.⁷ ............................................ B65D 83/06
(52) U.S. Cl. ........................... 128/203.15; 128/203.12; 128/203.21; 206/532
(58) Field of Search ............... 128/202.22, 203.12, 128/203.15, 203.21, 205.21; 604/58; 221/70, 221/73; 206/532, 534.1

(56) References Cited

U.S. PATENT DOCUMENTS

| | | | |
|---|---|---|---|
| 3,921,805 A | | 11/1975 | Compere |
| 4,778,054 A | * | 10/1988 | Newell et al. ............... 206/531 |
| 4,811,731 A | * | 3/1989 | Newell et al. .......... 128/203.15 |
| 5,349,947 A | * | 9/1994 | Newhouse et al. ..... 126/203.21 |
| 5,542,412 A | * | 8/1996 | Century ................. 128/203.15 |
| 5,622,166 A | * | 4/1997 | Eisele et al. ........... 128/203.12 |
| 6,006,747 A | * | 12/1999 | Eisele et al. ........... 128/203.15 |
| 6,098,619 A | * | 8/2000 | Britto et al. ........... 128/203.15 |
| 6,273,085 B1 | * | 8/2001 | Eisele et al. ........... 128/203.15 |
| 6,418,926 B1 | * | 7/2002 | Chawla .................. 128/203.12 |
| 2002/0092523 A1 | * | 7/2002 | Connelly et al. ....... 128/203.15 |

FOREIGN PATENT DOCUMENTS

| EP | 0938907 A | 9/1999 |
|---|---|---|
| WO | WO9834661 A | 8/1998 |

* cited by examiner

*Primary Examiner*—Henry Bennett
*Assistant Examiner*—Amanda Wieker
(74) *Attorney, Agent, or Firm*—James P. Riek

(57) ABSTRACT

A medicament pack comprising a first body portion having a pocket and a second body portion having an airpath. The pocket is sealed to a foil cover which connects to the second body portion. The second body portion is movable over the first body portion to break the seal and bring the pocket into communication with the airpath.

48 Claims, 8 Drawing Sheets

MEDICAMENT PACK

This application is filed pursuant to 35 USC 371 as a United States National Phase Application of Ser. No. PCT/EP00/09992 filed 11 Oct. 2000, which claims priority from GB 9924415.4 filed 16 Oct. 1999 in the United Kingdom.

TECHNICAL FIELD

The present invention relates to a medicament pack for incorporation into an inhalation device to enable administration of medicament to a patient.

BACKGROUND TO THE INVENTION

The use of inhalation devices in the administration of medicaments, for example in bronchodilation therapy, is well known.

Dry powder inhalation devices are known which comprise a body or housing within which a blister or pocket-containing medicament pack is located. Such medicament packs may comprise a base sheet in which the blister or pocket is formed and a lid sheet which covers the pocket/blister. Typically the drug is accessed from the blister or pocket by peeling back or rupturing a section of the lid sheet to expose the medicament within the blister/pocket. Rupturing the lid sheet may result in some fragmentation at the point of rupture. Inhalation devices which employ peeling mechanisms to remove the lid sheet avoid this potential problem. However such inhalation devices often require complicated internal mechanisms to peel the lid sheet away from the base sheet.

It is desirable that the inhalation device is simple for the user to operate. It is also desirable that dry powder inhalation devices are not too bulky so that the user may carry their device with them at all times, if required, and are not too embarrassed to use the device in public.

The Applicants have now developed an improved medicament pack from which medicament can be accessed by a simple peeling action not requiring the use of an inhalation device with a complicated internal mechanism.

The Applicants have also found that the medicament pack can be used in conjunction with an inhalation device which may be operated with one hand and requires the performance of a single step to access the medicament. The inhalation device is therefore simple to use and the one-handed action improves the ease of use for patients, particularly for children, the elderly and disabled.

A further advantage of the medicament pack is that it is adaptable so that it may contain a unit dose for use in a single use disposable inhaler or be a multi-dose pack containing a number of discrete doses without requiring an unacceptably large inhalation device. The size and bulk of the device is limited by the use of an integral mouthpiece which does not significantly protrude from the device.

WO 99/27987 describes a dry powder inhaler with a slider for incrementally advancing a blister disc and for moving a lifter up a ramp to rupture the blister. The device however is made up of many different components and has a complex structure.

SUMMARY OF THE INVENTION

According to one aspect of the present invention there is provided a medicament pack, the medicament pack comprising a first body portion having a pocket therein; a second body portion having an airpath therethrough; a foil forming a cover for said pocket and connecting with said second body portion; and a seal between said foil cover and the pocket, wherein the second body portion is movable over the first body portion to break said seal and bring the pocket into communication with the airpath.

Preferably the first body portion is a planar body. Preferably the second body portion is a planar body. Preferably the plane defined by the first and second planar body portions is shared.

Preferably the first body portion has an angled edge to assist movement of the second body portion thereover. Preferably said angled edge is cut at an angle of between 10° and 45° to the planar first body portion. Preferably the second body portion has an angled edge complementary to the angled edge of the first body portion to assist relative movement therebetween.

Preferably the first and second body portions are composed of materials selected from the group consisting of polyolefinics, polystyrenics, polyacetals, polycarbonates.

Preferably the medicament pack additionally has a join between the first and second body portions. Preferably said join includes a point of weakness to reduce the force required for movement of the second body portion over the first body portion.

Preferably the airpath includes a first and second passage through the second body portion. Preferably the flow of air is from the first passage through the pocket and out of the second passage. Preferably the first and second passages are parallel to each other.

Alternatively the first passage and second passages are perpendicular to each other.

Preferably the seal is formed by a sealing method selected from the group consisting of heat, laser, radio frequency, adhesive, staple, stamp and ultrasonic sealing. Preferably the seal is peelable.

Preferably the foil covers part of the second body portion. Preferably the foil is fixed to the second body portion. Preferably the foil is fixed to the second body portion by a method selected from the group consisting of heat, laser, radio frequency, adhesive, staple, stamp and ultrasonic sealing.

Preferably the medicament pack additionally has a tamper evident feature, that is to say a feature which provides evidence of any tampering with the medicament pack and its contents. Preferably the tamper evident feature comprises a tab joining the second body portion and the first body portion which is broken by movement of the second body portion over the first body portion.

Additionally, the foil seal acts as an indicator of tampering since it can not be resealed or restored following breakage of the seal or breakage of the foil cover.

Preferably the pocket contains medicament in powder form. Preferably the medicament is selected from the group consisting of albuterol, salmeterol, fluticasone propionate and beclomethasone dipropionate and salts or solvates thereof and any mixtures thereof.

According to another aspect of the invention there is provided a medicament pack in multi-dose form comprising a series arrangement of a plurality of medicament packs.

Preferably each of said plurality of medicament packs is connectable to an adjacent medicament pack in the series. Preferably in combination the plurality of medicament packs form a single planar body.

Preferably the planar body is disc-shaped. Preferably the disc-shaped planar body has a plurality of slots extending from its circumference through a portion of its radius, wherein each medicament pack is positioned between a neighboring pair of slots to allow movement thereof independently from the rest of the multi-dose pack.

Preferably the medicament pack is for use in an inhalation device.

According to another aspect of the present invention there is provided an inhalation device comprising a housing; a medicament pack as described hereinabove; a mounting for said medicament pack; an inhalation passage capable of communication with the airpath of said medicament pack; and a pinching mechanism for pinching the medicament pack to move the second body portion over the first body portion thereof.

Preferably the pinching mechanism comprises two sides of the housing which are movable relative to each other.

Alternatively the pinching mechanism comprises two movable pinch elements.

Alternatively the two movable pinch elements comprise a piston arrangement.

Alternatively the two movable pinch elements comprise levers.

Alternatively the two movable pinch elements comprise resilient arms. Preferably the resilient arms are biased towards the non-pinching position.

In one aspect the medicament pack is fixed to the mounting.

In another aspect the medicament pack is movable relative to the mounting.

Preferably the medicament pack is rotationally movable relative to the mounting.

Alternatively the medicament pack is slidably movable relative the mounting.

Preferably the mounting is a spindle.

Alternatively the mounting is a slide.

Preferably the multi-dose medicament pack additionally comprises an indexing mechanism to successively index each medicament pack in the series arrangement.

Preferably the indexing mechanism comprises a lever. Alternatively the indexing mechanism comprises a-resilient arm. Preferably the resilient arm is biased towards an at rest position.

Preferably the multi dose medicament pack additionally comprises a ratchet drive to allow indexing of the medicament pack in one direction only.

Preferably the inhalation device additionally comprises a mouthpiece which can communicate with the inhalation passage of the medicament pack.

Preferably the inhalation device additionally comprises tamper evident features, that is to say features which provide evidence of tampering with the inhalation device to access its contents. Preferably the tamper evident features comprise a mouthpiece cover which is snapped off before use of the inhalation device.

Preferably actuation of the pinching mechanism requires a single squeezing action capable of being performed with one hand.

BRIEF DESCRIPTION OF THE DRAWINGS

The invention will now be described with reference to the accompanying drawings in which:

FIG. 8d shows a perspective view of the medicament pack of FIG. 3 mounted on the device of FIG. 8a.

FIG. 8e shows a perspective view of the medicament pack of FIG. 3 mounted on the device of FIG. 8a.

DETAILED DESCRIPTION OF THE DRAWINGS

Figure 1:
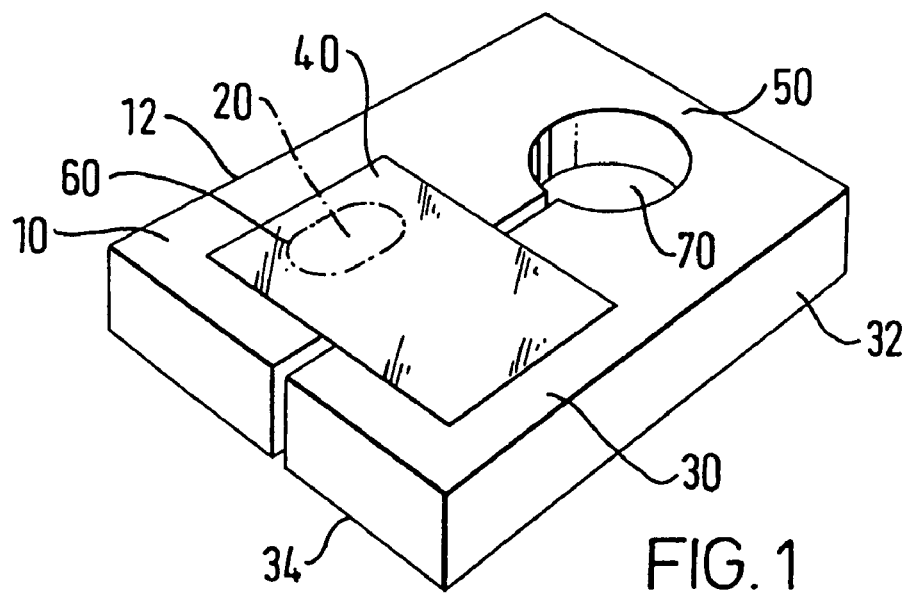
FIG. 1 shows a perspective view of a first medicament pack in accord with the present invention.

FIG. 1 shows a first medicament pack comprising a first body portion 10 containing a pocket 20 and a second body portion 30 containing an airpath (hidden). The pocket 20 on the first body portion 10 is covered by a foil cover 40 which extends to cover the second body portion 30. A seal 60 peelably seals the foil cover 40 to the pocket 20.

The first body portion 10 and second body portion 30 have a common joining portion 50 at one end. The common joining portion 50 has a circular section cut out of it to form a point of weakness 70.

The seal between the pocket and the foil may be broken and the pocket contents brought into communication with the airpath as follows. Exertion of an inward pressure at the side 12 of the first body portion 10 and at the side 32 of the second body portion 30 and of an upward pressure on the base 34 of the second body portion 30 results in the upward movement of the second body portion 30 followed by sideways movement across the top of the first body portion 10. The point of weakness 70 reduces the pressure required to move the second body portion 30 relative to the first body portion 10. The movement of the second body portion 30 over the first body portion 10 results in the seal 60 between the foil 40 and the pocket 20 breaking to allow the foil 40 to peel away from the pocket 20 to expose the pocket contents. The airpath of the second body portion 30 is brought into register with the pocket 20 to allow communication therebetween.

Figure 2:
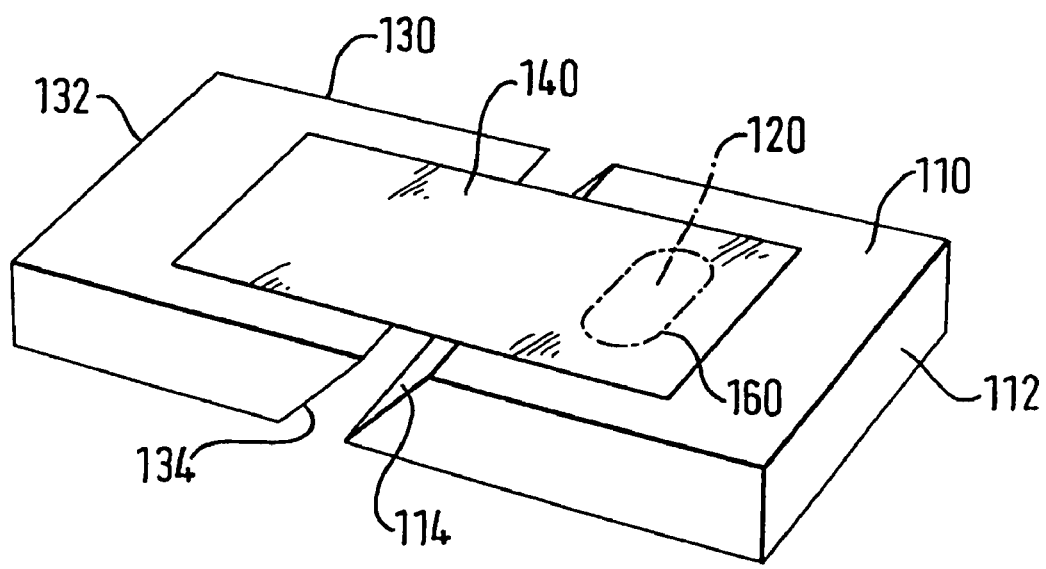
FIG. 2 shows a perspective view of a second medicament pack herein.

FIG. 2 shows a second medicament pack similar to the medicament pack of FIG. 1 comprising a first body portion 110 containing a pocket 120, positioned next to a second body portion 130 containing an airpath (hidden). The pocket 120 on the first body portion 110 is covered by a foil cover 140 which extends to cover the second body portion 130. A seal 160 peelably seals the foil cover 140 to the pocket 120. One side of the first body portion 110 is cut at an angle to form a ramp 114. The facing side 134 of the second body portion 130 is cut at a complementary angle to allow movement of the second body portion 130 up the ramp 114.

The seal between the pocket and the foil may be broken and the pocket contents brought into communication with the airpath as follows. Exertion of an inward pressure at the outer side 112 of the first body portion 110 and at the outer side 132 of the second body portion 130 results in movement of the second body portion 130 up the ramp 114 and across the top of the first body portion 110. This movement of the second body portion 130 over the first body portion 110 results in the seal between the foil 160 and the pocket 120 breaking to allow the foil 160 to peel away from the pocket 120 to expose the pocket contents. The airpath of the second body portion 130 aligns with the pocket 120 to allow the contents to be inhaled.

Figure 3:
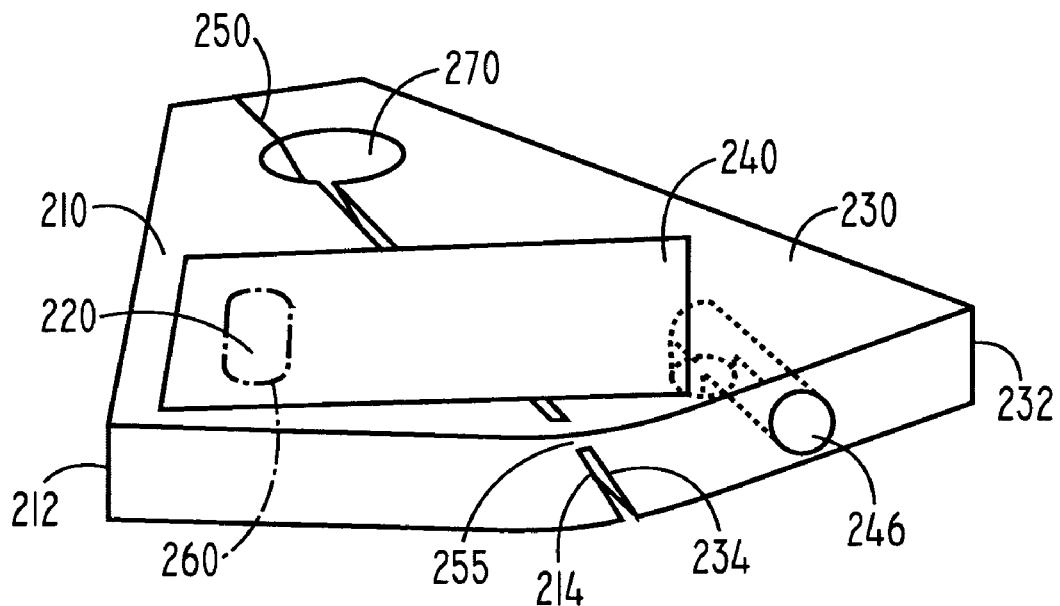
FIG. 3 shows a perspective view of a third medicament pack herein.

FIG. 3 shows a third medicament pack similar to the medicament packs of FIGS. 1 and 2 comprising a first body portion 210 containing a pocket 220 positioned next to a second body portion 230 containing an airpath (hidden). The pocket 220 on the first body portion 210 is covered by a piece of foil 240 which extends to cover the second body portion 230. A seal 260 peelably seals the foil cover 240 to the pocket 220. One side of the first body portion 210 is cut at an angle to form a ramp 214. The facing side 234 of the second body portion 230 is cut at a complementary angle to allow movement of the second body portion 230 up the ramp 214. The first body portion 210 and second body portion 230 have a common joining portion 250 at one end. The common joining portion 250 has a circular section cut out of it to form a point of weakness 270 to further ease movement of the body portions 210, 230. At the opposite end of the first and second body portions to the point of weakness is a tab 255 which joins a small section of the body portions together but is snapped upon movement of the second body portion over the first body portion. The tab acts as evidence of any tampering with the medicament pack.

The seal between the pocket and the foil may be broken and the pocket contents brought into communication with the airpath as follows. Exertion of an inward pressure at the outer side of the first body portion 212 and at the outer side of the second body portion 232 results in movement of the second body portion 230 up the ramp 214 and across the top of the first body portion 210. This movement of the second body portion 230 over the first body portion 210 results in the seal between the foil 260 and the pocket 220 breaking to allow the foil 260 to peel away from the pocket 220 to expose the pocket contents. The airpath of the second body portion 230 aligns with the pocket 220 to allow the contents to be inhaled.

Figure 4A:
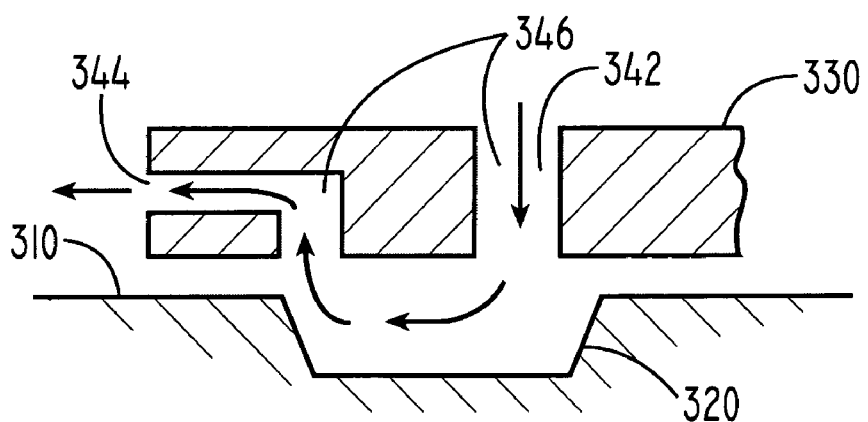
FIG. 4a shows a sectional view of an airpath suitable for use with the medicament pack of FIGS. 1, 2 and 3 but not exclusive thereto.
Figure 4B:
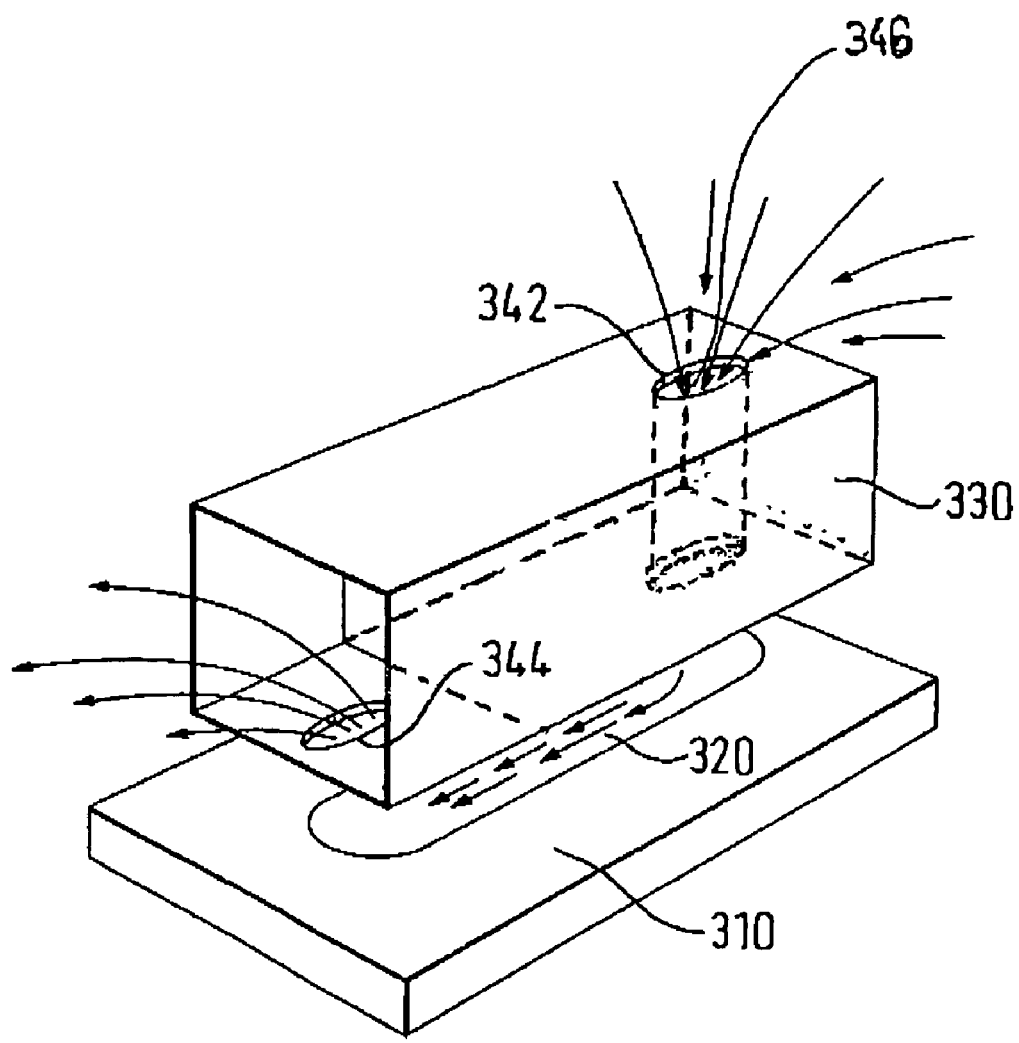
FIG. 4b shows a perspective view of an airpath suitable for use with the medicament pack of FIGS. 1, 2 and 3 but not exclusive thereto.

FIG. 4a shows a sectional view of a first and second body portion and FIG. 4b a perspective view of a first and second body portion to show the preferred route of the airpath 346 through the second body portion 330. The airpath 346 comprises an air inlet passage 342 and an air outlet passage 344. When the second body portion 330 has been moved over the first body portion 310, the airpath 346 is aligned with the pocket 320. The user of an inhalation device, within which the first and second body portions 310, 330 are contained, inhales in order to deliver the powdered medicament to their lungs. The air is drawn from the air inlet passage 342, through the pocket 320 and then carries the powdered medicament with it out through the air outlet passage 344 and through a mouthpiece of the inhalation device into the lungs of the user.

Figure 5A:
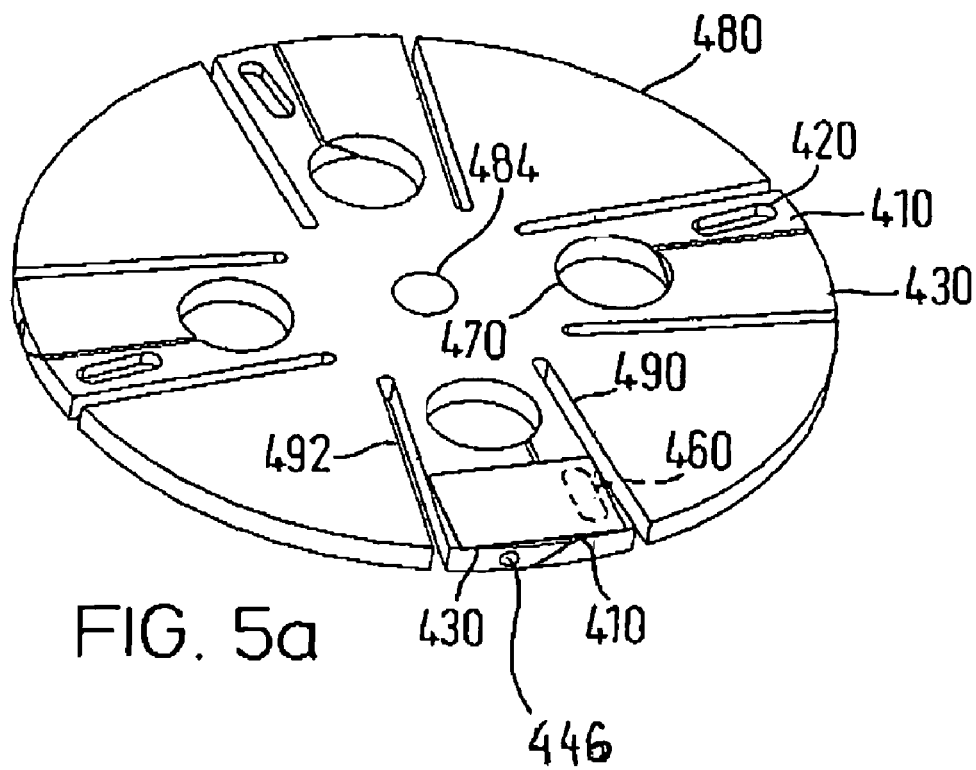
FIG. 5a shows a perspective view of a fourth medicament pack herein.
Figure 5B:
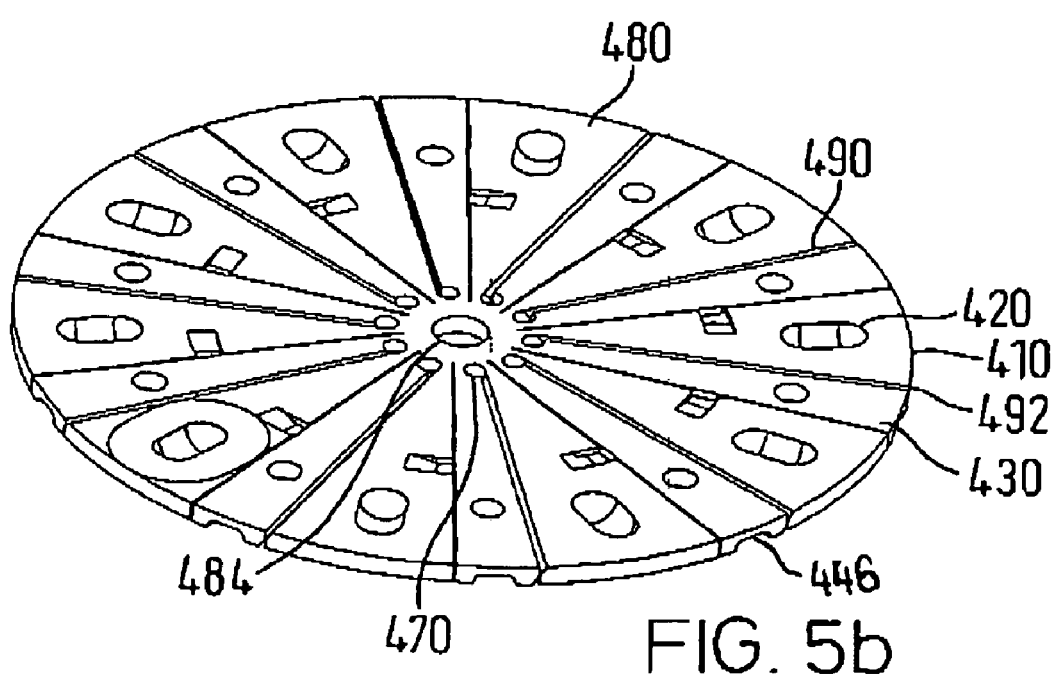
FIG. 5b shows a perspective view of a fifth medicament pack herein.

FIGS. 5a and 5b show a 4-dose and 10-dose series arrangement of the medicament pack shown in FIG. 3 in a disc 480. Each first and second body portion 410, 430 are situated between a pair of slots 490, 492 which extend from the circumference of the disc 480 along the length of the body portions 410, 430. The slots 490, 492 allow the first and second body portions 410, 430 to move independently from the rest of the disc 480. Pressure may be exerted at the slots 490, 492 to move a second body portion 430 over the first body portion 410 of the same single pack to break the seal and allow the contents of the pocket 420 to be inhaled via the airpath 446. Between the inner end of each first and second body portion is cut circular section to form a point of weakness 470 to further ease movement of the body portions 410, 430. The disc 480 has a central hole 484 to allow it to be a mounted in an inhalation device.

Figure 6:
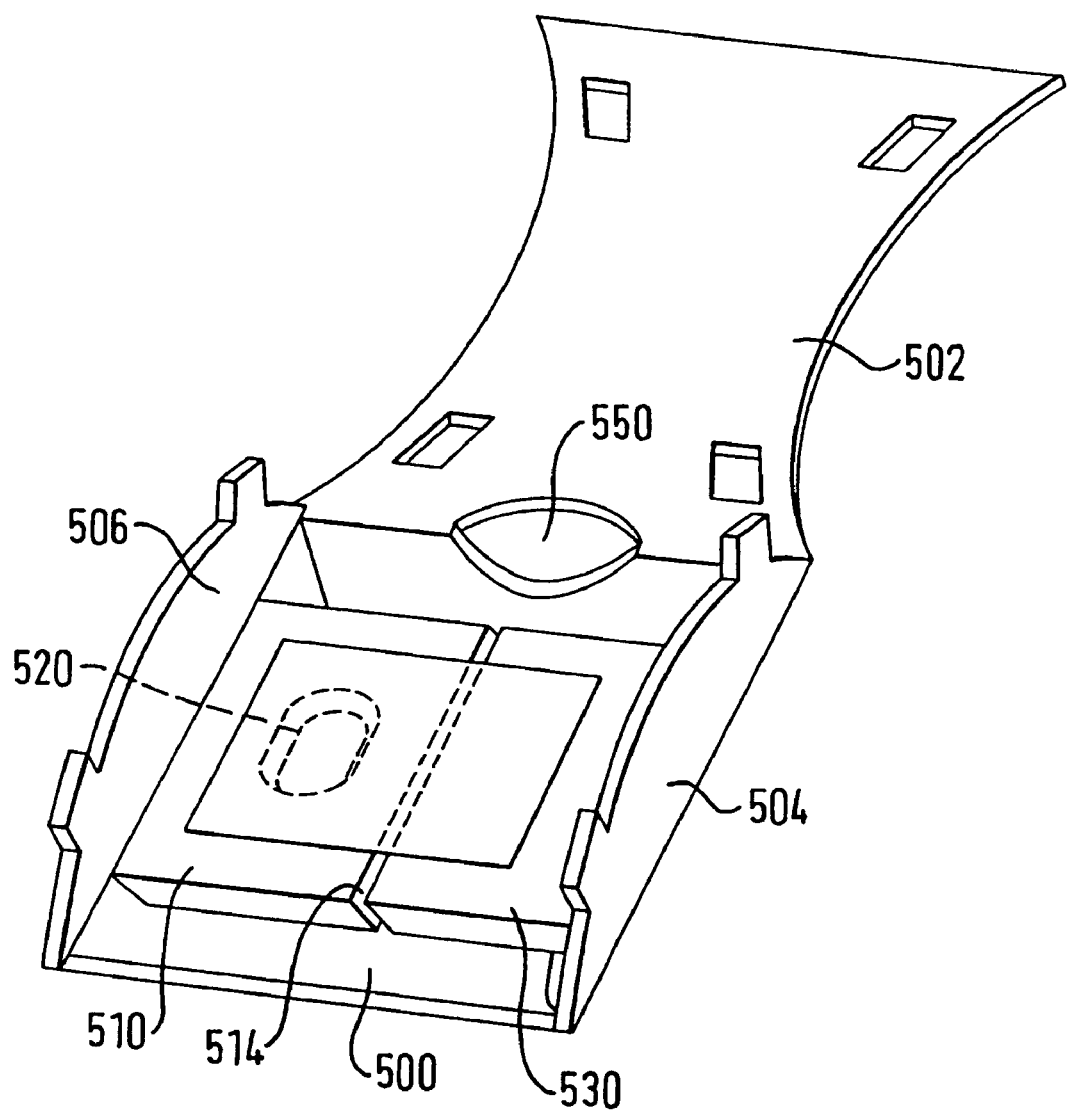
FIG. 6 shows a perspective view of a first inhalation device in accord with the present invention.

FIG. 6 shows an inhalation device comprising a housing 500 and a single dose medicament pack. The medicament pack may form an integral part of the device or be mounted within the housing 500. The inhalation device is shown with the lid 502 open so that the medicament pack inside can be seen, however the lid 502 would be folded over and fixed to the rest of the housing 500 to enclose the medicament pack. The medicament pack comprises a single first body portion 510 containing a foil-covered pocket 520 and a single second body portion 530 containing an airpath (hidden). The side walls 504, 506 of the housing 500 are flexible. Pinching the side walls 504, 506 of the housing 500 together pushes the second body portion 530 up the ramp 514 on the first body portion 510 and along the first body portion 510 until the foil seal has broken and the pocket 520 aligned with the airpath ready for inhalation. The housing 500 includes a mouthpiece 550 through which the user can inhale to deliver the drug to their lungs. The mouthpiece 550 may have a cover (not shown), which must be snapped off the housing 500 prior to use. The mouthpiece cover seals the device and acts as evidence of tampering.

Figure 7:
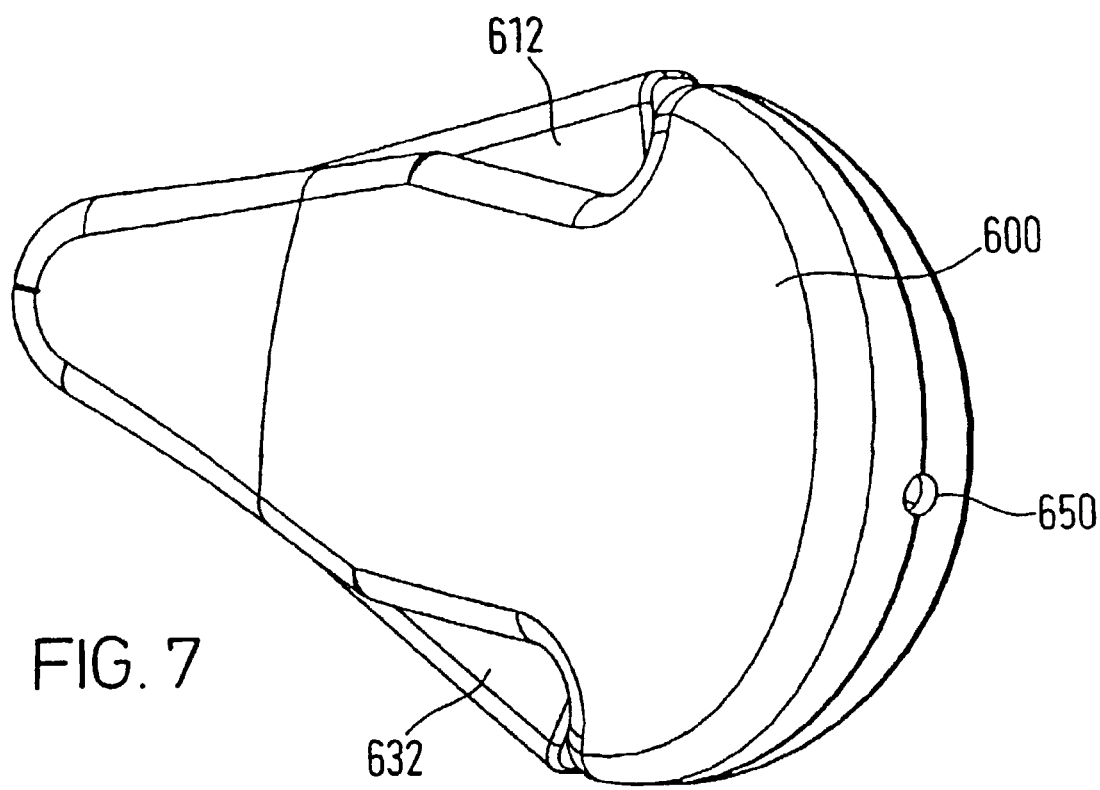
FIG. 7 shows a perspective view of a second inhalation device herein.

FIG. 7 shows a second inhalation device comprising a housing 600 and a single dose medicament pack. The outer edges 612, 632 of the first and second body portions 610, 630 protrude through the housing 600 and can be pinched together to move the second body portion over the first body portion to break the foil and bring the airpath into communication with the pocket. The housing 600 includes a mouthpiece 650 through which the user can inhale to deliver the drug to their lungs. The mouthpiece 650 may have a cover (not shown), which must be snapped off the housing 600 prior to use. The mouthpiece cover seals the device and acts as evidence of tampering.

Figure 8A:
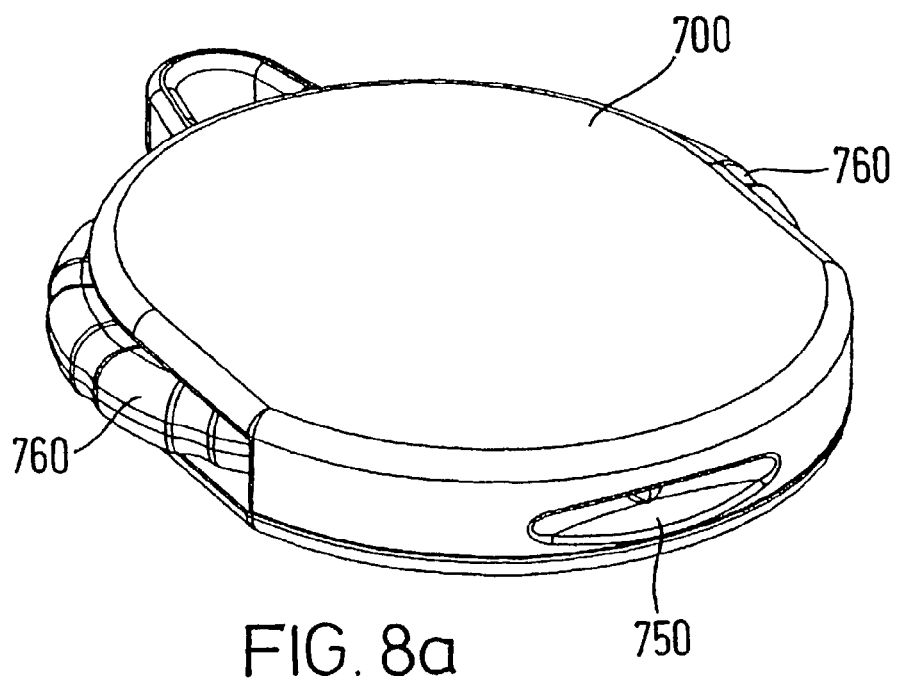
FIG. 8a shows a perspective view of a third inhalation device herein.

FIG. 8a shows a third inhalation device comprising a housing 700, a mouthpiece 750 and a pinch mechanism 760. Contained within the housing is mounting for a multi-dose medicament pack and a ratchet drive which connects to the base of the multi dose pack.

Figure 8B:
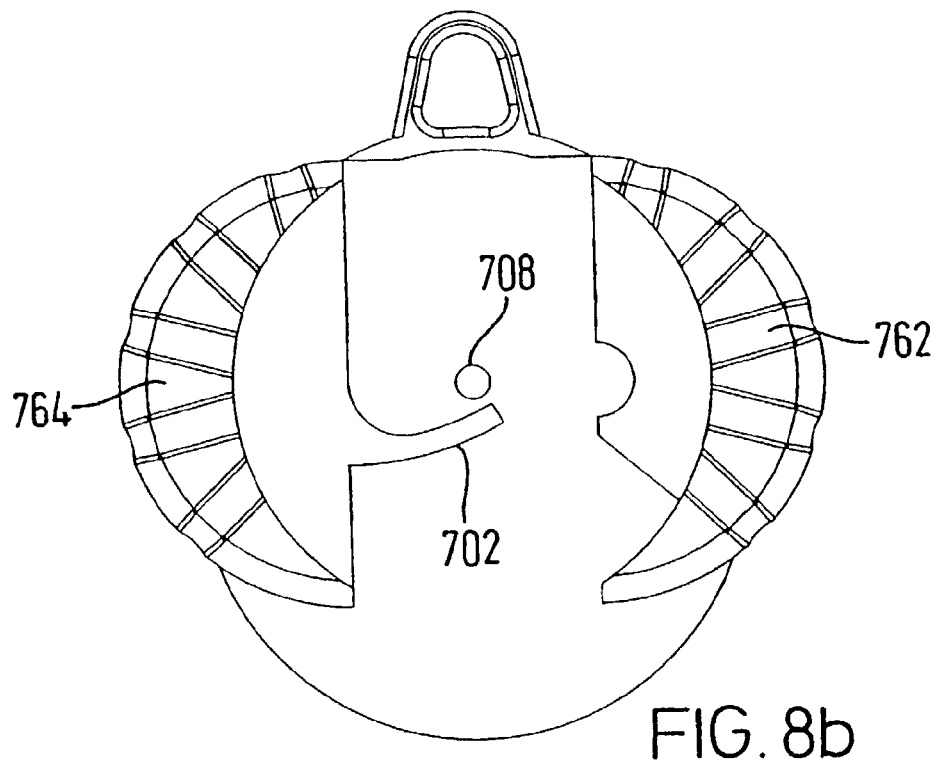
FIG. 8b shows a perspective view of the internal mechanism of the device of FIG. 8a at rest.
Figure 8C:
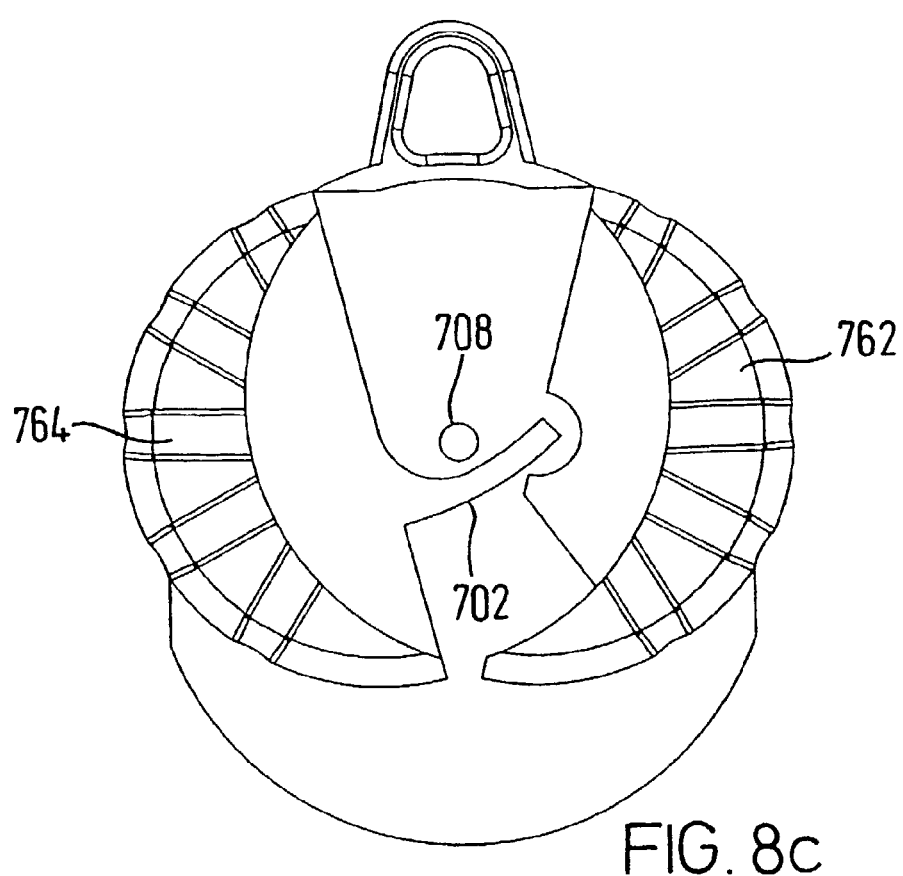
FIG. 8c shows a perspective view of the internal mechanism of the device of FIG. 8b when pinched.

FIGS. 8b and 8c show the inhalation device of FIG. 8a without the outer housing 700 to enable the inner features to be seen.

The pinching mechanism comprises two pinch levers 762, 764 which are shown in the at-rest position in FIG. 8b. The pinch levers 762, 764 are sprung so that they are biased towards the at-rest position with the levers pushed out. A medicament pack can be loaded onto the central mounting 708 when the pinch levers 764, 764 are in the at-rest position.

FIG. 8c shows the position of the levers 762, 764 when they have been pinched. One pinch lever 762 indexes the medicament pack when released from the pinched position using the ratchet drive 702, which connects to the base of the medicament pack.

Figure 8D:
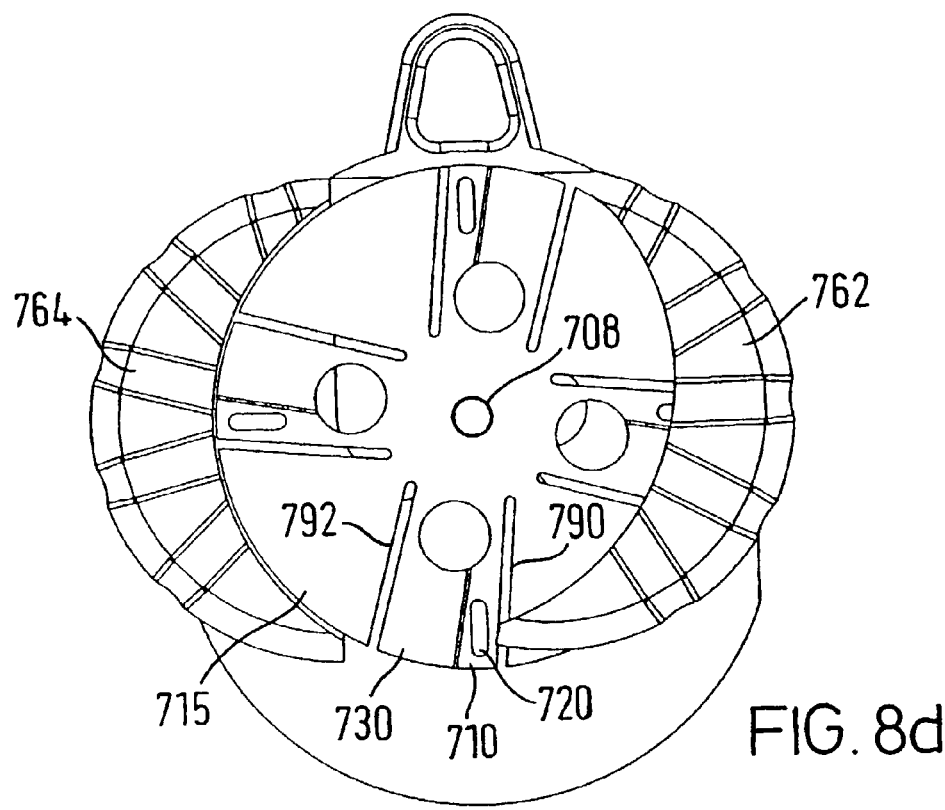
Figure 8E:
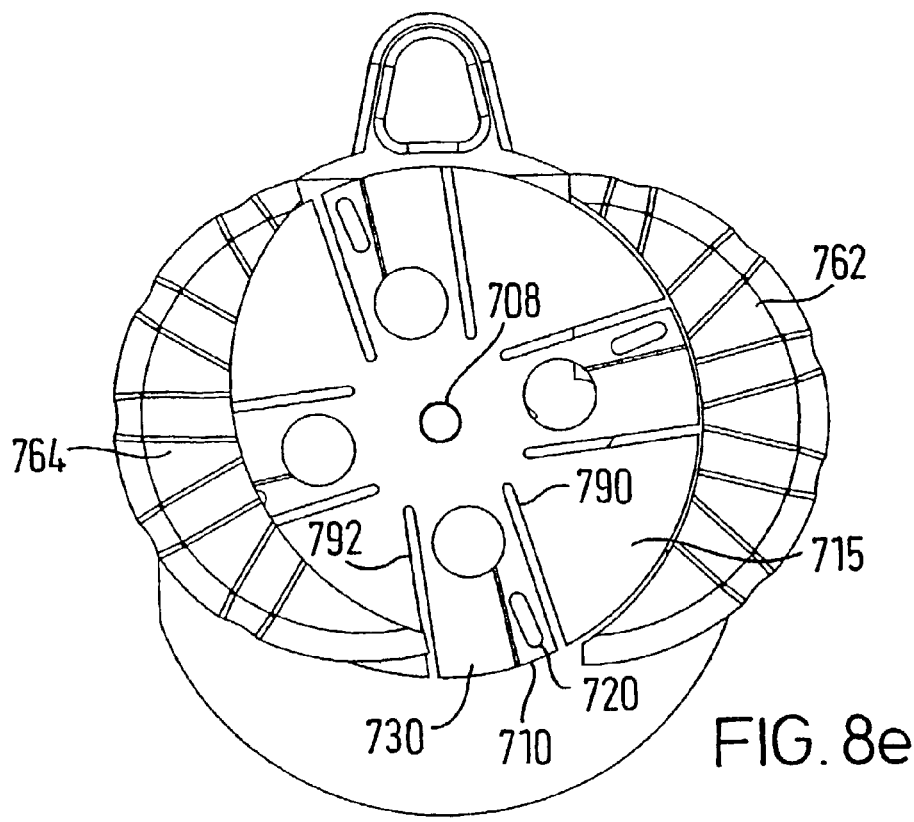

FIGS. 8d and 8e show the medicament pack of FIGS. 8b and 8c with a medicament pack mounted onto the device. When the pinch levers 762, 764 are squeezed together, the end of the first pinch lever 762 inserts into a slot 790 in the medicament pack 715 next to a first body portion 710 and indexes the pack into a central position, rotating it about the mounting 708. At the same time the second pinch lever 764 moves over the medicament pack 715 until it locates into the slot 792 next to the second body portion 730 of the same single pack. The second pinch lever 764 provides an opposing force to the first pinch lever 762 which pinches the medicament pack 715 to move the second body portion 730 over the first body portion 710 to break the foil seal over the pocket 720 and align the pocket 720 with the airpath ready for inhalation by the user through the mouthpiece 750 of the device.

Following inhalation, the pinch levers 762, 764 are released and spring back to the at-rest position shown in FIG. 8b. As the pinch levers 762, 764 move back to the at-rest position, the first pinch lever 762 indexes the used pocket 720 away from the central position by engagement of the ratchet drive 702 on the pinch lever 762 with the underside of the medicament pack.

It may be appreciated that any of the parts of the pack which contact the medicament suspension may be coated with materials such as fluoropolymer materials which reduce the tendency of medicament to adhere thereto. Any movable parts may also have coatings applied thereto which enhance their desired movement characteristics. Frictional coatings may therefore be applied to enhance frictional contact and lubricants used to reduce frictional contact as necessary.

The medicament dispenser of the invention is suitable for dispensing medicament for the treatment of respiratory disorders such as disorders of the lungs and bronchial tracts including asthma and chronic obstructive pulmonary disorder (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone eg as the furoate ester), ciclesonide, triamcinolone (eg as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine: bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[ (3H)-benzothiazolone; adenosine 2a agonists, eg 2R,3R,4S,5R)-2-[6-Amino-2-(1S-hydroxymethyl-2-phenyl-et 4-(aminocarbonyl)-1-piperidinyl]carbonyl}oxy) phenyl]-2-[((2S)-4-methyl-2-{[2-(2-m potassium salt), diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

What is claimed is:

1. A medicament pack comprising
a first body portion having a pocket therein;
a second body portion having an airpath therethrough;
a foil forming a cover for said pocket and connecting with said second body portion;
and a seal between said foil cover and the pocket;
wherein the first body portion and the second body portion are slidably movable relative to each other from a first position wherein the first and second body portions are laterally distanced from each other and said airpath of said second body portion is not vertically aligned with said pocket in the first body portion, to a second position wherein said airpath of said second body portion is aligned with said pocket of the first body portion, said movement from said first position to said second position causing said pocket to be exposed to said airpath.

2. A medicament pack according to claim 1 wherein the first body portion is a planar body.

3. A medicament pack according to claim 1 wherein the second body portion is a planar body.

4. A medicament pack according to claim 3 wherein the plane defined by the first and second planar body portions is shared.

5. A medicament pack according to claim 1 wherein the first body portion has an angled edge to assist in slidable movement of the second body portion thereover.

6. A medicament pack according to claim 5 wherein said angled edge is cut at an angle of between 10° and 45° to the planar first body portion.

7. A medicament pack according to claim 5 wherein the second body portion has an angled edge complementary to the angled edge of the first body portion to assist relative movement therebetween.

8. A medicament pack according to claim 1 wherein the first and second body portions are composed of materials selected from the group consisting of polyolefinics, polystyrenics, polyacetals, polycarbonates.

9. A medicament pack according to claim 1 additionally comprising a joining portion between the first and second body portions.

10. A medicament pack according to claim 9 wherein said joining portion includes a point of weakness to reduce the force required for movement of the second body portion over the first body portion.

11. A medicament pack according to claim 1 wherein the airpath includes a first and second passage through the second body portion.

12. A medicament pack according to claim 11 wherein the flow of air is from the first passage through the pocket and out of the second passage.

13. A medicament pack according to claim 11 wherein the first and second passages are perpendicular to each other.

14. A medicament pack according to claim 1 wherein the seal is formed by a sealing method selected from the group consisting of heat, laser, radio frequency, adhesive, staple, stamp and ultrasonic sealing.

15. A medicament pack according to claim 1 wherein the seal is peelable.

16. A medicament pack according to claim 1 wherein the foil covers part of the second body portion.

17. A medicament pack according to claim 16 wherein the foil is fixed to the second body portion.

18. A medicament pack according to claim 17 wherein the foil is fixed to the second body portion by a method selected from the group consisting of heat, laser, radio frequency, adhesive, staple, stamp and ultrasonic sealing.

19. A medicament pack according to claim 1 additionally comprising a tamper evident feature.

20. A medicament pack according to claim 19 wherein the tamper evident feature comprises a tab joining the second body portion and the first body portion which is broken by movement of the second body portion over the first body portion.

21. A medicament pack according to claim 1 wherein the pocket contains medicament in powder form.

22. A medicament pack according to claim 21 wherein medicament is selected from the group consisting of albuterol, salmeterol, fluticasone propionate and beclomethasone dipropionate and salts or solvates thereof and any mixtures thereof.

23. A medicament pack in multi-dose form comprising a series arrangement of a plurality of medicament packs according to claim 1.

24. A medicament pack according to claim 23 wherein each of said plurality of medicament packs is connectable to an adjacent medicament pack in the series.

25. A medicament pack according to claim 23 wherein in combination the plurality of medicament packs form a single planar body.

26. A medicament pack according to claim 25 wherein said planar body is disc-shaped.

27. A medicament pack according to claim 26 wherein the disc-shaped planar body has a plurality of slots extending from its circumference through a portion of its radius, wherein each medicament pack is positioned between a neighboring pair of slots to allow movement thereof independently from the rest of the multi-dose pack.

28. A medicament pack according to claim 1 for use in an inhalation device.

29. An inhalation device comprising
a housing;
a medicament pack according to claim 1;
a mounting for said medicament pack;
an inhalation passage capable of communication with the airpath of said medicament pack; and
a pinching mechanism for pinching the medicament pack to move the second body portion over the first body portion thereof.

30. An inhalation device according to claim 29 wherein the pinching mechanism comprises two sides of the housing which are movable relative to each other.

31. An inhalation device according to claim 30 wherein the pinching mechanism comprises two movable pinch elements.

32. An inhalation device according to claim 31 wherein said two movable pinch elements comprise resilient arms.

33. An inhalation device according to claim 32 wherein said resilient arms are biased towards the non-pinching position.

34. An inhalation device according to claim 29 wherein the medicament pack is fixed to the mounting.

35. An inhalation device according to claim 29 wherein the medicament pack is movable relative to the mounting.

36. An inhalation device according to claim 35 wherein the medicament pack is rotationally movable relative to the mounting.

37. An inhalation device according to claim 35 wherein the mounting is a spindle.

38. An inhalation device according to claim 29 wherein the medicament pack is in multi-dose form, additionally comprising an indexing mechanism to successively index each medicament pack in the series arrangement.

39. An inhalation device according claim 38 wherein the indexing mechanism comprises a lever.

40. An inhalation device according to claim 29 additionally comprising a mouthpiece in communication with the inhalation passage.

41. An inhalation device according to claim 29 additionally comprising tamper evident features.

42. An inhalation device according to claim 29 wherein actuation of the pinching mechanism requires a single squeezing action capable of being performed with one hand.

43. A medicament pack comprising
a first body portion having a pocket therein:
a second body portion having an airpath therethrough;
a foil forming a cover for said pocket and connecting with said second body portion;
and a seal between said foil cover and the pocket;
wherein the second body portion is movable over the first body portion to break said seal and bring the pocket into communication with the airpath, and wherein said first body portion has an angled edge to assist movement of the second body portion thereover, and said second body portion has an angled edge complementary to the angled edge of the first body portion to assist relative movement therebetween.

44. A medicament pack comprising
a first body portion having a pocket therein;
a second body portion having an airpath therethrough, wherein the airpath includes a first and second passage through the second body portion;
a foil forming a cover for said pocket and connecting with said second body portion;
and a seal between said foil cover and the pocket;
wherein the second body portion is movable over the first body portion to break said seal and bring the pocket into communication with the airpath.

45. A medicament pack according to claim 44 wherein the flow of air is from the first passage through the pocket and out of the second passage.

46. A medicament pack according to claim 44 wherein the first and second passages are parallel to each other.

47. A medicament pack according to claim 44 wherein the first and second passages are perpendicular to each other.

48. An inhalation device comprising
   (a) a housing;
   (b) a medicament pack comprising
      (i) a first body portion having a pocket therein;
      (ii) a second body portion having an airpath therethrough;
      (iii) a foil forming a cover for said pocket and connecting with said second body portion; and
      (iv) a seal between said foil cover and the pocket; wherein the second body portion is movable over the first body portion to break said seal and bring the pocket into communication with the airpath; and wherein the medicament pack is in multi-dose form
   (c) a mounting for said medicament pack;
   (d) an inhalation passage capable of communication with the airpath of said medicament pack; and
   (e) a pinching mechanism for pinching the medicament pack to move the second body portion over the first body portion thereof, and
   (f) additionally comprising an indexing mechanism to successively index each medicament pack in the series arrangement, wherein the indexing mechanism comprises a lever.

* * * * *